(12) United States Patent
Henke et al.

(10) Patent No.: US 11,617,811 B2
(45) Date of Patent: Apr. 4, 2023

(54) STERILE CONTAINER COMPRISING A VAPOUR-PERMEABLE SEAL

(71) Applicant: AESCULAP AG, Tuttlingen (DE)

(72) Inventors: Matthias Henke, Fridingen (DE); Katrin Sternberg, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 427 days.

(21) Appl. No.: 16/643,730

(22) PCT Filed: Sep. 4, 2018

(86) PCT No.: PCT/EP2018/073694
§ 371 (c)(1),
(2) Date: Mar. 2, 2020

(87) PCT Pub. No.: WO2019/048410
PCT Pub. Date: Mar. 14, 2019

(65) Prior Publication Data
US 2020/0268920 A1    Aug. 27, 2020

(30) Foreign Application Priority Data
Sep. 6, 2017   (DE) ..................... 10 2017 120 520.9

(51) Int. Cl.
*B65D 51/16*    (2006.01)
*A61L 2/20*     (2006.01)
(Continued)

(52) U.S. Cl.
CPC .............. *A61L 2/208* (2013.01); *A61B 50/30* (2016.02); *A61L 2/202* (2013.01); *A61L 2/204* (2013.01);
(Continued)

(58) Field of Classification Search
CPC .................... B65D 51/16; B65D 65/38; B65D 2543/00435; B65D 2565/388;
(Continued)

(56) References Cited

U.S. PATENT DOCUMENTS 5,127,523 A     7/1992   Herdlicka
6,247,609 B1 *  6/2001   Gabele .................... A61L 2/26
                                                    220/912

(Continued)

FOREIGN PATENT DOCUMENTS

CN       87107584 A     4/1988
CN        1193500 A     9/1998
(Continued)

OTHER PUBLICATIONS

German Search Report for German Application No. 10 2017 120 520.9, with English translation, dated May 4, 2018, 11 pages.
(Continued)

*Primary Examiner* — Luan K Bui
(74) *Attorney, Agent, or Firm* — Christopher A. Rothe; Culhane Meadows, PLLC

(57) ABSTRACT

A sterile container includes a container pan, a container cover, a closure for closing the sterile container, and a seal or sealing element between the container pan and the container cover. The seal or sealing element is vapor-permeable.

7 Claims, 1 Drawing Sheet

(51) Int. Cl.
  *A61B 50/30* (2016.01)
  *A61L 2/26* (2006.01)
  *B65D 65/38* (2006.01)
  *A61B 50/00* (2016.01)
  *B65D 43/02* (2006.01)

(52) U.S. Cl.
  CPC ............ *A61L 2/206* (2013.01); *A61L 2/26* (2013.01); *B65D 51/16* (2013.01); *B65D 65/38* (2013.01); *A61B 2050/0067* (2016.02); *A61L 2202/182* (2013.01); *A61L 2202/23* (2013.01); *B65D 43/0212* (2013.01); *B65D 2543/00435* (2013.01); *B65D 2565/388* (2013.01)

(58) Field of Classification Search
  CPC ... A61B 50/30; A61B 2050/0067; A61L 2/26; A61L 2202/182
  USPC ............ 206/363–366, 369, 370, 438, 439; 220/203.1, 203.23–203.28
  See application file for complete search history.

(56) References Cited

U.S. PATENT DOCUMENTS

| | | | |
|---|---|---|---|
| 8,430,261 B2 * | 4/2013 | Eggenreich | B60K 15/0406 220/203.23 |
| 9,393,074 B2 | 7/2016 | Praedel et al. | |
| 9,649,399 B2 | 5/2017 | Weisshaupt et al. | |
| 9,895,456 B2 | 2/2018 | Verschuur | |
| 10,183,089 B2 | 1/2019 | Kitamura | |
| 2006/0076081 A1 | 4/2006 | Gleichauf et al. | |
| 2011/0226762 A1 | 9/2011 | Mermet | |
| 2012/0202000 A1 | 8/2012 | Bricker et al. | |
| 2014/0144799 A1 * | 5/2014 | Praedel | A61B 50/34 206/438 |
| 2014/0346072 A1 * | 11/2014 | Jacobson | A61B 50/33 53/449 |
| 2015/0217008 A1 | 8/2015 | Zwingenberger et al. | |
| 2015/0306259 A1 | 10/2015 | Deutschle et al. | |
| 2017/0360975 A1 * | 12/2017 | White | B01D 46/0005 |
| 2019/0001050 A1 | 1/2019 | Okihara | |
| 2019/0038788 A1 | 2/2019 | Thomas et al. | |

FOREIGN PATENT DOCUMENTS

| | | |
|---|---|---|
| CN | 2678592 Y | 2/2005 |
| CN | 2800010 Y | 7/2006 |
| CN | 2817841 Y | 9/2006 |
| CN | 101687053 A | 3/2010 |
| CN | 202044540 U | 11/2011 |
| CN | 104220794 A | 12/2014 |
| CN | 104602739 A | 5/2015 |
| CN | 104837510 A | 8/2015 |
| CN | 105000281 A | 10/2015 |
| CN | 105163766 A | 12/2015 |
| CN | 107029264 A | 8/2017 |
| DE | 2312382 A1 | 9/1974 |
| DE | 3933177 A1 | 4/1991 |
| DE | 19851239 A1 | 5/2000 |
| DE | 20118911 U1 | 2/2002 |
| DE | 10118860 C1 | 9/2002 |
| DE | 102008053301 A1 | 4/2010 |
| DE | 102009011435 A1 | 8/2010 |
| DE | 102012111096 A1 | 5/2014 |
| DE | 102016101912 A1 | 8/2017 |
| EP | 0513614 A1 | 11/1992 |
| WO | 0222178 A1 | 3/2002 |
| WO | 2014109011 A1 | 7/2014 |
| WO | 2017075000 A1 | 5/2017 |

OTHER PUBLICATIONS

International Search Report and Written Opinion for International Application PCT/EP2018/073694, dated Dec. 7, 2018, 10 pages.
Chinese Office Action received in Application No. 201880055256.9 dated Dec. 31, 2020, 25 pages.
German Office Action received in Application No. 10 2017 120 520.9 dated Jun. 16, 2020. (with translation).
Office Action received in Chinese Application No. 201880055256.9 dated Feb. 15, 2022, with translation, 19 pages.
Office Action received in Chinese Application No. 201880055256.9 dated Jul. 5, 2021, with translation, 29 pages.

* cited by examiner

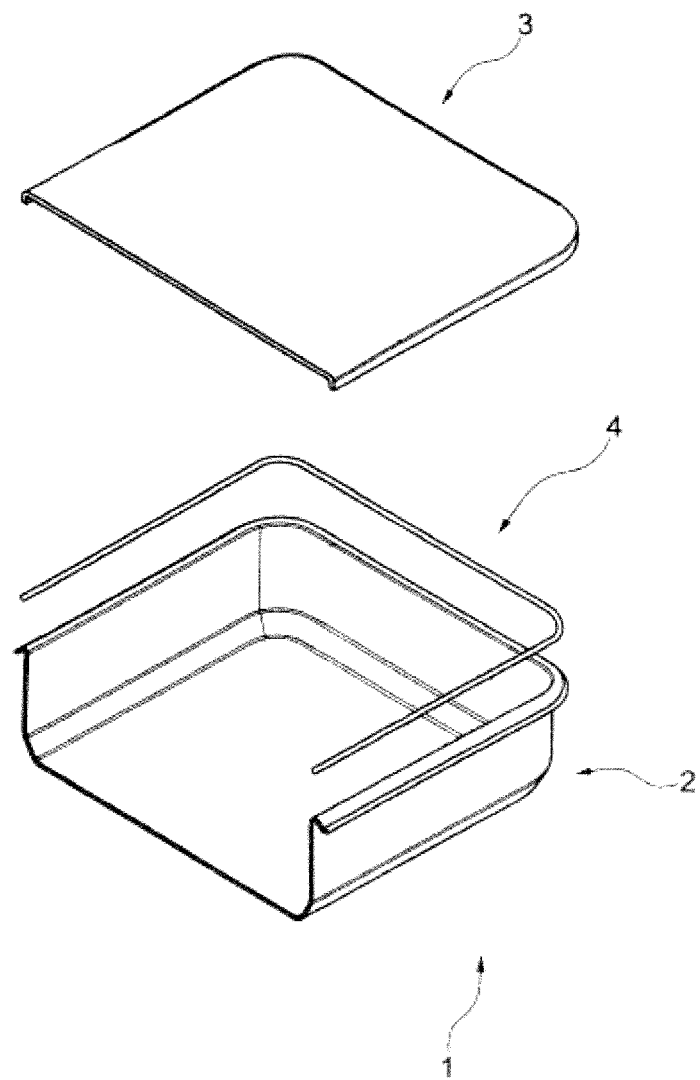

STERILE CONTAINER COMPRISING A VAPOUR-PERMEABLE SEAL

CROSS-REFERENCE TO RELATED APPLICATIONS

This application is the United States national phase entry of International Application No. PCT/EP2018/073694, filed Sep. 4, 2018, which claims the benefit of priority of German Application No. 10 2017 120 520.9, filed Sep. 6, 2017. The contents of International Application No. PCT/EP2018/073694 and German Application No. 10 2017 120 520.9 are incorporated by reference herein in their entireties.

FIELD

The present invention relates to a sterile container comprising a vapor-permeable seal as well as to a vapor-permeable seal for use with a sterile container.

Conventional sterile containers have a sterile container pan, a sterile container cover and a media exchange system. The media exchange system is used in particular for the exchange of liquid and/or gaseous media, such as water vapor, and can be designed as a filter, valve or similar. The media exchange system thus also serves to balance the pressure between the interior of the sterile container and the external environment. The sterile container pan and the sterile container cover are connected by a seal/sealing element. The sealing element serves to seal the space between the sterile container pan and the sterile container cover against fluids that could otherwise pass through this space, thus shielding the interior of the sterile container from the environment. The closure is either provided on the pan, on the cover or on both, or is separate from the sterile container. In many cases, a silicone round cord or a silicone lip gasket is used as seal/sealing element. The media exchange system, be it a valve or a filter system or a combination of both, is conventionally arranged in the pan or in the lid.

The seal/sealing element of conventional sterile containers is subject to wear. In particular, foamed silicone round cords become brittle over their lifetime and lose their restoring force, which is why a visual inspection of the seal/sealing element must be carried out before each use of a sterile container. In addition, before each use of the sterile container, in addition to the seal/the sealing element, the media exchange system of the sterile container must also be checked for its integrity and functionality by means of a rather complex visual inspection.

SUMMARY

The present invention is therefore based on the task of providing a sterile container which only requires a shortened/simplified visual inspection.

This task is solved by integrating or combining the functions of the seal/sealing element and the media exchange system in one component. In other words, the invention provides that the seal/sealing element and the media exchange system are present in combined form. In known sterile containers, the media exchange system and the sealing element or seal between the container pan and the container cover are two separate components.

The construction of the sterile container according to the present invention is thus simplified, and instead of two components, namely the seal/sealing element and the media exchange system, only one component in which the functions of the seal/sealing element and the media exchange system are combined, has to be subjected to visual inspection. The media exchange system in the form of e.g. a filter or valve can therefore be omitted in the case of a sterile container according to the invention. A sterile container according to the invention can therefore be designed without any valve or filter.

It is preferred that the vapor-permeable seal/sealing element is selectively or exclusively permeable to water vapor. Furthermore, the permeability may be only unidirectional.

The vapor-permeable seal is preferably located between the container cover and the container pan. An advantage of this arrangement is that the vapor-permeable seal/sealing element between the container cover and the container pan is well protected against unwanted damage. Conventional media exchange systems of conventional sterile containers are usually accessible from above on the container cover if no additional covers, auxiliary lids or similar are provided, and can therefore be easily damaged.

In principle, however, it would also be possible to equip the container cover and/or the container pan at least in sections with the vapor-permeable seal. The vapor-permeable seal could thus also be integrated into the container cover and/or the container pan, for example as a kind of window made of a vapor-permeable seal material which is embedded in a wall section of the container pan or the container cover. In this case, however, a conventional seal would be required in the space between the container pan or container cover.

The vapor-permeable seal/sealing element forms a microbial barrier according to one aspect of the invention and at the same time allows a gas exchange to take place between the inside and outside of the container. The microbial barrier guarantees the sterility of any sterile goods in the sterile container even over a longer period of time. The possibility of gas exchange also outside the sterilizer is particularly important during storage and transport in order to enable pressure equalization between the interior and exterior of the container.

According to another aspect of the invention, the vapor-permeable seal is designed as a disposable component/throwaway component. This has the additional advantage that the vapor-permeable seal/sealing element does not have to be visually inspected for its integrity or functionality before reusing the sterile container. The visual inspection is thus further simplified or shortened.

Alternatively, the vapor-permeable seal/sealing element may also be designed as a reusable component/permanent component. In this case, the vapor-permeable seal/sealing element must be checked for its integrity and functionality by a visual inspection before the sterile container is used again, but the functional integration of the seal/sealing element and media exchange system eliminates the need for a separate media exchange system, so that in contrast to conventional sterile containers, only one component (the vapor-permeable seal/sealing element) instead of two components (seal/sealing element and media exchange system) must be visually inspected.

According to another aspect of the invention, the vapor-permeable seal/sealing element is manufactured from a porous material, preferably from porous polytetrafluoroethylene (PTFE). This is particularly suitable for the reusable concept.

In particular with the disposable concept, the sealing element may also be manufactured from polypropylene, fleece and sterilization paper. Cords, packages etc. can also be suitable as long as the material can withstand the conditions of sterilization.

According to another aspect of the invention, the vapor-permeable seal is therefore designed as a cord, package, fabric, knitted mesh or fleece.

According to a further aspect of the invention, the vapor-permeable seal is configured as a sealing lip, which is designed to open a passage for pressure compensation, preferably a gap between the container pan and the container cover, by elastic deformation in the event of negative pressure in the interior of the sterile container. The lip geometry of the sealing lip is selected here such that the sealing lip opens the passage for pressure compensation between the container pan and the container cover at a predetermined threshold value of the negative pressure in the interior of the sterile container.

According to another aspect of the invention, the closure of the sterile container is spring-mounted. This enables sufficient pressure compensation even with strong pressure changes in the interior of the sterile container. If there is a high overpressure in the interior of the sterile container, the container cover can yield resiliently.

Another aspect of the present invention relates to a vapor-permeable seal/sealing element which is designed to be used with a sterile container. For example, such a vapor-permeable seal could be used to retrofit an existing conventional sterile container.

Such a vapor-permeable seal/sealing element forms a microbial barrier according to one aspect of the invention.

Preferably, the vapor-permeable seal/sealing element is designed as disposable component/throwaway component. However, the vapor-permeable seal/sealing element can also be a reusable component/permanent component.

A vapor-permeable seal/sealing element according to the invention is preferably manufactured from a porous material, in particular from polytetrafluoroethylene.

A vapor-permeable seal/sealing element according to the invention is preferably designed as cord, package, fabric, knitted mesh or fleece.

A vapor-permeable seal/sealing element according to the invention can also be designed as a sealing lip, which deforms in a predetermined way depending on a pressure gradient, especially when a defined negative pressure is reached.

BRIEF DESCRIPTION OF THE DRAWING FIGURE

The FIGURE is an exploded perspective view of a sterile container according to one embodiment.

DETAILED DESCRIPTION

A possible configuration of the present invention is shown in the FIGURE. The sketch is for illustration purposes only.

As shown in the FIGURE, a sterile container 1 has a container pan 2 and a container cover 3. Not shown is the closure, which may be provided either on the container cover, the container pan or on both, or formed to be independent and separate from the sterile container. The pan and cover geometry is arbitrary.

In the exploded illustration shown, the vapor-permeable seal 4 is shown, which is arranged between the container pan 2 and the container cover 3. Once the sterile container is assembled, the vapor-permeable seal 4 lies flush between the container cover 3 and the container pan 2 and seals the space between these two parts.

In order to ensure sufficient pressure equalization even during strong pressure changes in the sterilizer (if equalization via the seal alone is not sufficient), the closure can be spring-mounted so that the cover can be lifted in the event of excess pressure in the container.

In order to enable pressure equalization even in the event of negative pressure in the container, the seal could be designed in the form of a lip geometry in which the lip "folds away" in the event of negative pressure in the container and opens a gap through which pressure equalization can take place. The seal can be formed, for example, in the form of cords, packings, woven fabrics, knitted meshes and nonwovens.

The core of the invention lies in a combination of media exchange system and seal in one component, preferably a vapor-permeable seal/sealing element, in a sterile container, either as a disposable product or for reuse.

In the case of a disposable product, the visual inspection of the seal, which is otherwise designed as a permanent product, is not necessary. In addition, all components of the media exchange system are omitted.

If designed as a reusable product, all components of the media exchange system are omitted, but the visual inspection must be carried out on the combined component, preferably the vapor-permeable seal/sealing.

The invention claimed is:

1. A sterile container comprising:
   a container pan;
   a container cover; and
   a vapor-permeable seal for sealing an interior of the sterile container from an environment,
   the vapor-permeable seal being provided between the container pan and the container cover,
   wherein the vapor-permeable seal is selectively permeable to water vapor, forms a microbial barrier, and is manufactured from a porous material, and
   wherein the vapor-permeable seal is configured as a sealing lip designed to open a passage for pressure compensation by elastic deformation in response to a negative pressure in the interior of the sterile container.

2. The sterile container according to claim 1, wherein the vapor-permeable seal is a disposable component.

3. The sterile container according to claim 1, wherein the vapor-permeable seal is designed as a cord, package, fabric, knitted mesh or fleece.

4. The sterile container according to claim 1, wherein the vapor-permeable seal is selectively permeable to one or more sterilization media.

5. The sterile container according to claim 4, wherein the vapor-permeable seal is selectively permeable to one or more of hydrogen peroxide, ethylene oxide, ozone and formaldehyde.

6. The sterile container according to claim 1, wherein the vapor-permeable seal is manufactured from porous polytetrafluoroethylene.

7. The sterile container according to claim 1, wherein the passage is a gap between the container pan and the container cover.

* * * * *